United States Patent
Josse et al.

(10) Patent No.: US 10,829,788 B2
(45) Date of Patent: Nov. 10, 2020

(54) MULTIPLE TANK HIGH SOLIDS ANAEROBIC DIGESTER

(71) Applicant: ANAERGIA INC., Burlington (CA)

(72) Inventors: Juan Carlos Josse, Aliso Viejo, CA (US); Christian Friedl, Aichach (DE); Martin Bayer, Buchbach (DE)

(73) Assignee: ANAERGIA INC., Burlington (CA)

( * ) Notice: Subject to any disclaimer, the term of this patent is extended or adjusted under 35 U.S.C. 154(b) by 97 days.

(21) Appl. No.: 15/628,189

(22) Filed: Jun. 20, 2017

(65) Prior Publication Data

US 2017/0283833 A1     Oct. 5, 2017

Related U.S. Application Data

(62) Division of application No. 14/352,477, filed as application No. PCT/CA2011/001315 on Nov. 30, 2011, now Pat. No. 9,719,111.

(Continued)

(51) Int. Cl.
*C12P 5/02*     (2006.01)
*C12M 1/00*     (2006.01)
(Continued)

(52) U.S. Cl.
CPC .............. *C12P 5/023* (2013.01); *C02F 3/286* (2013.01); *C02F 3/2866* (2013.01); *C02F 11/04* (2013.01);
(Continued)

(58) Field of Classification Search
CPC .. C12P 5/023; C12P 1/00; C02F 11/04; C02F 3/286; C02F 3/2866; C02F 2209/005;
(Continued)

(56) References Cited

U.S. PATENT DOCUMENTS 2,430,519 A * 11/1947 Mallory ................ C02F 3/1247
                                                                210/605
4,323,367 A     4/1982 Ghosh
(Continued)

FOREIGN PATENT DOCUMENTS

DE     102007005069 A1     7/2008
EP          1930404 A1      6/2008
(Continued)

OTHER PUBLICATIONS

Machine Translation of DE102007005069. (Year: 2019).*
(Continued)

*Primary Examiner* — Michael L Hobbs
(74) *Attorney, Agent, or Firm* — Borden Ladner Gervais LLP; Scott Pundsack

(57) ABSTRACT

A multi-stage anaerobic digester is designed to treat a high solids, stackable feedstock. The system may also receive a pumpable feedstock such as a slurry or sludge. In a first stage, the digestate circulates in one direction around a raceway such that the digestate may pass a feed inlet multiple times before leaving the first tank. An optional side stream loop withdraws fibrous material from near the top of the raceway and return digestate with chopped fibers, preferably lower and further along the raceway. An outlet from the raceway located near, but upstream of, the feed inlet discharges partially digested substrate to a second stage, which is operated as a stirred tank reactor. The two stages may be provided in a single tank with an internal wall separating a ring shaped outer portion from a cylindrical inner portion. The digester may be operated in a thermophilic temperature range.

16 Claims, 3 Drawing Sheets

Related U.S. Application Data

(60) Provisional application No. 61/548,919, filed on Oct. 19, 2011.

(51) Int. Cl.
*C02F 3/28* (2006.01)
*C02F 11/04* (2006.01)
*C12M 1/107* (2006.01)
*C12P 1/00* (2006.01)

(52) U.S. Cl.
CPC ............ *C12M 21/04* (2013.01); *C12M 23/34* (2013.01); *C12M 23/58* (2013.01); *C12M 29/02* (2013.01); *C12M 29/18* (2013.01); *C12P 1/00* (2013.01); *C02F 2209/005* (2013.01); *C02F 2209/42* (2013.01); *C02F 2209/44* (2013.01); *C02F 2301/02* (2013.01); *C02F 2303/10* (2013.01); *Y02E 50/343* (2013.01); *Y02W 10/23* (2015.05); *Y02W 10/30* (2015.05)

(58) Field of Classification Search
CPC ............ C02F 2209/42; C02F 2209/44; C02F 2301/02; C02F 2301/10; C12M 21/04; C12M 23/34; C12M 23/58; C12M 29/02; C12M 29/18; Y02W 10/23; Y02W 10/30; Y02E 50/343
USPC .................... 435/303.1, 290.1–290.4; 47/1.4
See application file for complete search history.

(56) References Cited

U.S. PATENT DOCUMENTS

| | | | |
|---|---|---|---|
| 5,275,722 A * | 1/1994 | Beard | C02F 3/1257 210/195.1 |
| 6,342,378 B1 | 1/2002 | Zhang et al. | |
| 6,342,387 B1 | 1/2002 | Hayashizaki et al. | |
| 6,592,762 B2 * | 7/2003 | Smith | C02F 3/18 210/605 |
| 6,982,035 B1 | 1/2006 | O'Keefe | |
| 2002/0105855 A1 * | 8/2002 | Behnke | B01F 5/0206 366/167.1 |
| 2006/0076291 A1 * | 4/2006 | Wells | C02F 3/28 210/603 |
| 2006/0289356 A1 * | 12/2006 | Burnett | C02F 11/04 210/603 |
| 2009/0170184 A1 | 7/2009 | Shepherd et al. | |

FOREIGN PATENT DOCUMENTS

| | | | |
|---|---|---|---|
| FR | 2481874 | A1 | 11/1981 |
| SU | 1599320 | * | 10/1990 |
| WO | 2008034153 | A1 | 3/2008 |
| WO | 2008128631 | A2 | 10/2008 |

OTHER PUBLICATIONS

European Patent Application No. 11874294.9, Office Action dated Sep. 5, 2018.
European Patent Application No. 11874294, Supplementary European Search Report dated Apr. 23, 2015.
International Patent Application No. PCT/CA2011/001315, International Preliminary Report on Patentability dated May 1, 2014.
International Patent Application No. PCT/CA2011/001315, International Search Report and Written Opinion dated May 15, 2012.
Machine translation of FR2481874, translated on Feb. 3, 2016.
Patterson et al. Greimel Biogas Plants, Gruntegernbach, Bavaria, Germany, University of Glamorgan, 2009.
U.S. Appl. No. 14/352,477, Notice of Allowance dated Mar. 22, 2017.
European Patent Application No. 11874294.9, Office Action dated Dec. 2, 2019.

* cited by examiner

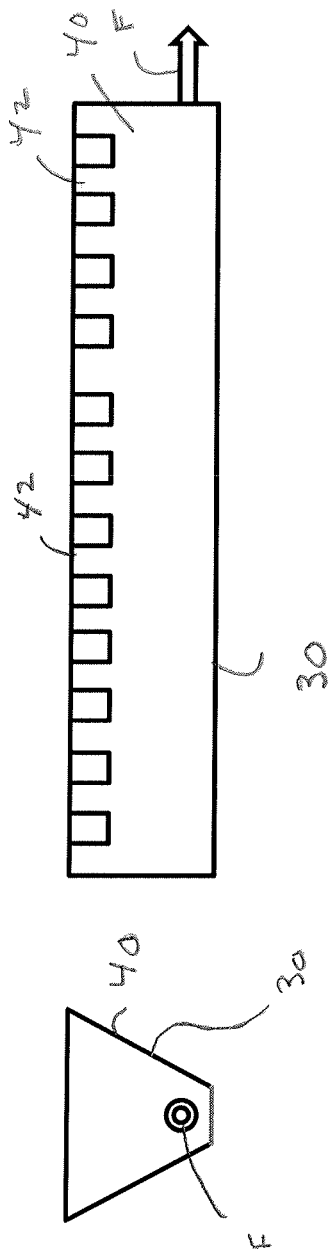

MULTIPLE TANK HIGH SOLIDS ANAEROBIC DIGESTER

CROSS-REFERENCE TO RELATED APPLICATIONS

This application is a division of U.S. Pat. No. 9,719,111; filed Dec. 10, 2014 which is a National Stage Entry of International Application No. PCT/CA2011/001315, filed Nov. 30, 2011, which is a non-provisional application of U.S. Application Ser. No. 61/548,919, filed Oct. 19, 2011. U.S. Application Ser. No. 61/548,919 is incorporated by reference.

FIELD

This specification relates to anaerobic digestion.

BACKGROUND

Anaerobic digestion is typically done in a single tank or in two tanks connected in series. The tanks are typically cylindrical and mixed so as to operate as a continuously stirred tank reactor (CSTR). Where two tanks are used, the effluent from the upstream tank flows to the downstream tank. In some cases, two tanks are used to separate the process into an acid phase and a gas or methanogenic phase. In such a phased digestion system, the volume of the acid phase tank is much lower than that of the gas phase tank.

INTRODUCTION TO THE INVENTION

Some types of feedstock to an anaerobic digester have such a high solids concentration that the feedstock cannot be pumped. These types of feedstock, referred to as stackable feedstock, may be still be transferred to an anaerobic digester but they are very difficult to mix. The feedstock could be diluted, but this would require a source of water for dilution, increase the size of digester required, and lower the reaction rate in the digester. An anaerobic digestion system described in this specification is designed to treat a high solids feedstock with minimal, if any, dilution. Optionally, the system may receive a pumpable feedstock such as a slurry or sludge alone or in combination with a stackable substrate.

The system comprises two digester stages that operate in series. In a first stage, substrate being digested in the digester, called digestate, circulates in one direction around an endless loop, alternatively called a raceway. The digestate may flow around the raceway and pass by a feed inlet multiple times before leaving the first stage. An inlet to a passageway from the first stage to the second stage is preferably located near, but upstream of, the feed inlet. Partially digested substrate flows to the second stage, which is operated as a stirred reactor.

Optionally, a side stream mixing loop may withdraw digestate with fibrous material from near the free surface of the digestate, chop the fibers, and return the digestate with chopped fibers to a lower elevation within the digestate. An inlet to the side stream mixing loop may comprise a crust breaker.

The two stages of the digester may be constructed within a single circular tank. An internal wall separates a ring shaped outer portion from a cylindrical inner portion of the tank. The outer ring provides the first stage, where partial digestion occurs. The internal cylindrical portion is the second stage of the digester, where the digestion is completed. The solids content and viscosity in the first stage are higher than in the second stage as a result of partial digestion of the volatile solids in the feedstock in the first stage. With further digestion in the second stage, the solids content and viscosity of the digestate are further reduced, facilitating mixing. A portion of the digestate from the second stage tank can be recirculated to the first stage tank if needed to reduce the solids content with difficult-to-digest feedstocks.

The process is not primarily intended to separate the digester into an acid phase and a gas or methanogenic phase, but rather to facilitate mixing with high solids content feedstocks. Accordingly, the volume of the first stage tank may be 40% or more, or 40 to 50%, of the total digester volume. The first stage of the digester, with flow in one direction around a path or raceway, is able to process very high-solids feedstocks with minimal or no dilution. Reduced dilution allows digestion to occur in a shorter hydraulic retention time, which in turn allows for a lower digester volume for a given feed rate.

The tank-in-tank configuration described above may be more difficult to construct than a single tank but it creates a compact two stage reactor since there is no space lost in between the two portions of the tank. Heat losses are also reduced since the internal concrete wall insulates the contents of the second stage digester. The digester may operate in a thermophilic temperature range. Accordingly, the tank-in-tank configuration could be advantageous in two stage digesters generally, particularly large digesters. Large digesters may include digesters that, when fed maize silage at 30 to 35% DS, make enough biogas to produce of 500 kW or more, or 800 kW or more, of electricity with a gas engine generator that is about 40% efficient in converting the gas to electricity.

BRIEF DESCRIPTION OF THE DRAWINGS

FIG. 3A is a side view of a crust breaker of the anerobic digestion system of FIG. 1.

FIG. 3B is a front view of the crust breaker of FIG. 3A.

DETAILED DESCRIPTION

Figure 1:
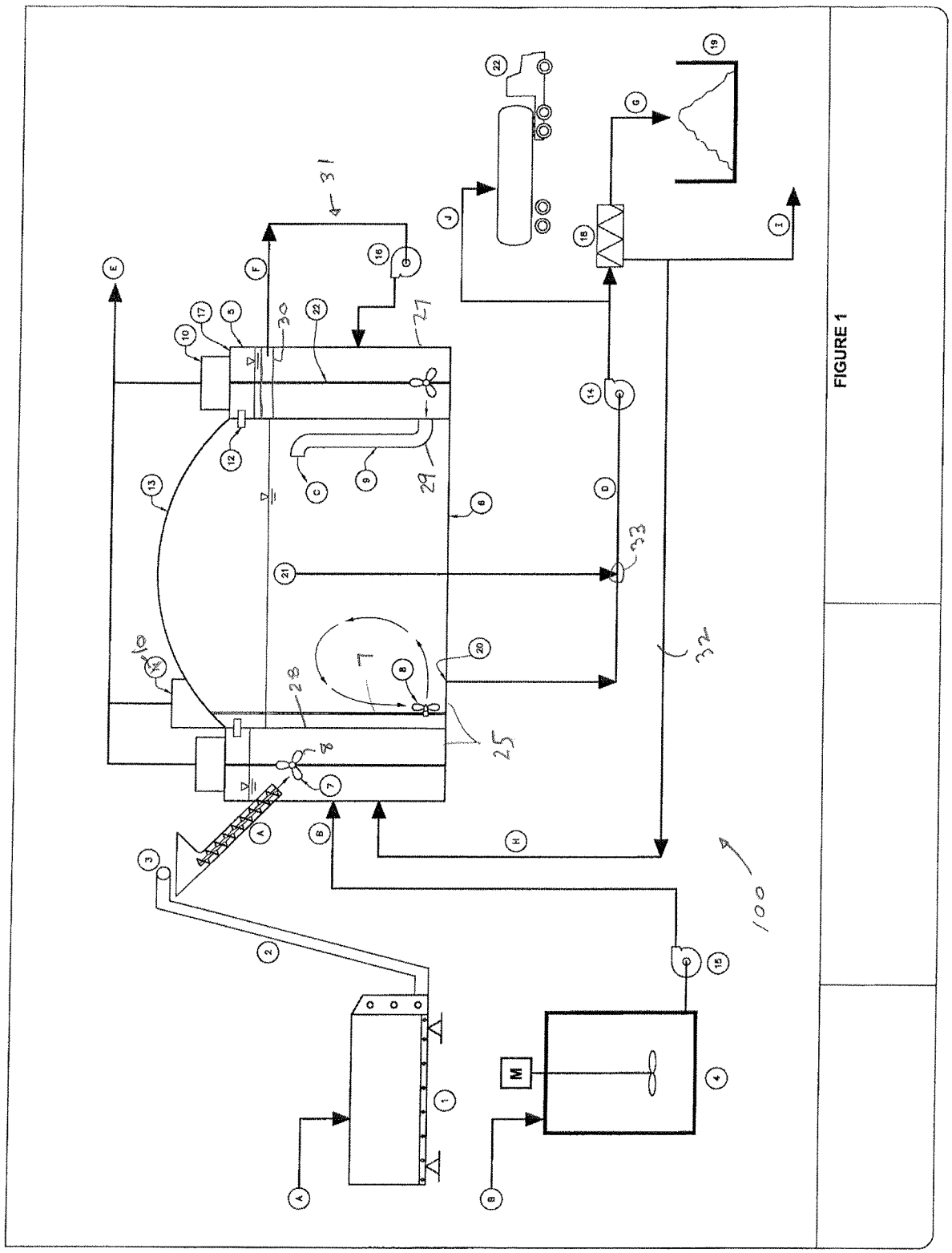
FIG. 1 is a schematic elevation view of an anaerobic digestion system.
Figure 2:
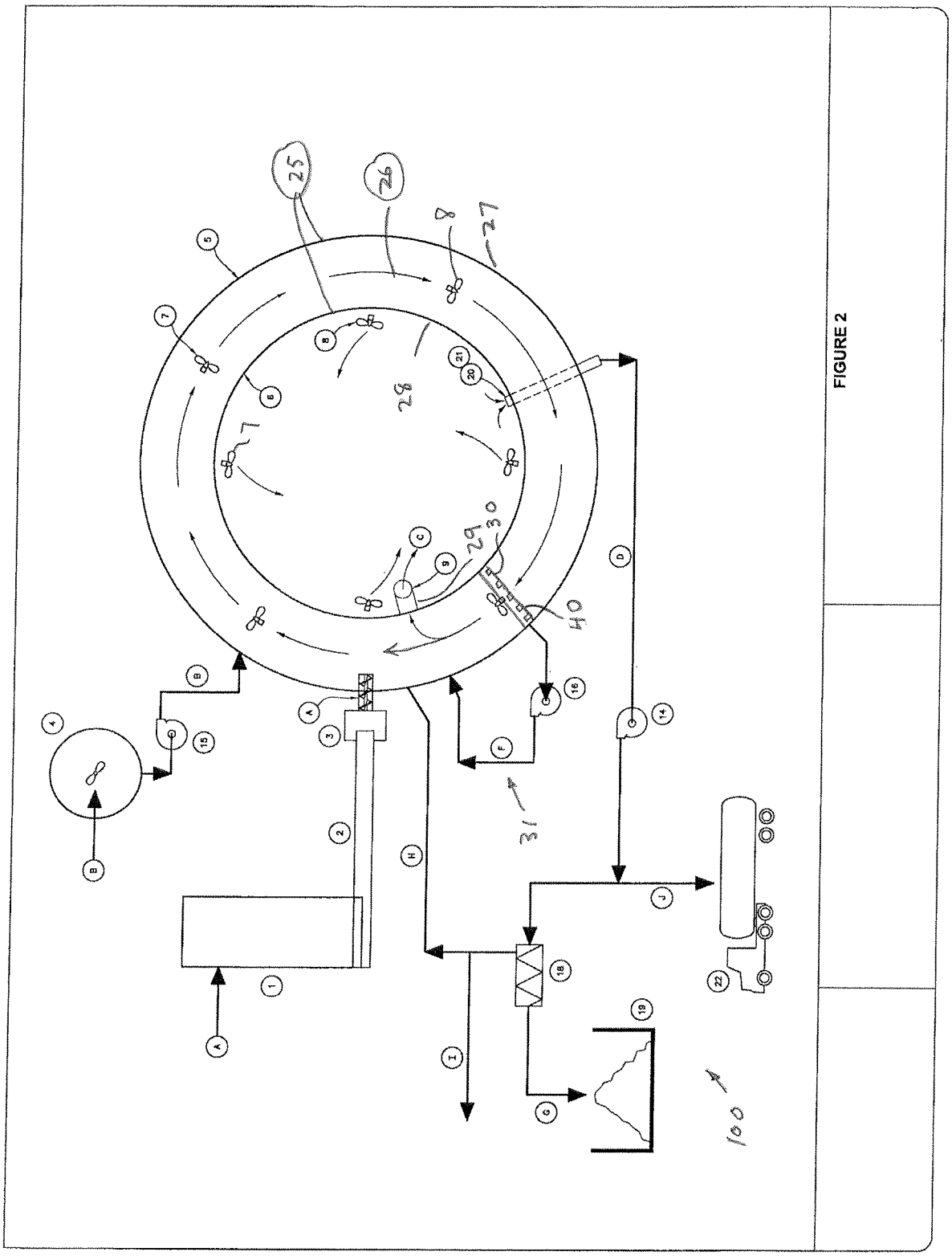
FIG. 2 is a schematic plan view of the anaerobic digestion system of FIG. 1.

FIGS. 1 and 2 show an anaerobic digestion system 100. The system 100 is able to digest an organic feedstock (alternatively called a substrate) with a high solids content that is stackable and not pumpable. Stackable feedstocks include, without limitation, silage from maize, grass, wheat or other grains, high solids manures such as from poultry layers, ensilaged sugar cane leaves or other crop residuals, dewatered sugar beet pulp cake, sugar cane processing filter cake, sugar cane ensilaged leaves, grape pomace, fruit peels and other high solids substrates from the food processing and meat processing industry, and wet distillers grain from the bioethanol industry. The system 100 can also digest a pumpable feedstock, and combinations of a stackable feedstock with a pumpable feedstock, such as a liquid substrate, a slurry or a sludge.

The system 100 in FIG. 1 consists of digester (25) having two stages connected in series. In the digester (25), both stages are contained within a covered cylindrical tank (27). An internal wall (28) separates a ring shaped outer portion of the tank (27) which provides a first stage (5), from a cylindrical inner portion of the tank (27) which provides the second stage (6). The inner and outer portions of tank (27) may also be referred to as inner and outer tanks, with a shared common wall, or as a tank within a tank. The first stage (5) provides a flow path in the form of an endless loop, or raceway. The second stage (6) provides an undivided mixing area. A passageway (29) allows partially digested substrate to flow through the internal wall (28), from the first stage (5) to the second stage (6). Digestion is started in the first stage (5) and completed in the second stage (6).

Other tank configurations might also be used. For example, a first stage tank may be located separate from a second stage tank. A first stage tank might also have another shape that creates a raceway. For example, a rectangular tank, preferably with semi-circular ends, can be fitted with a lengthwise divider.

The first stage (5) operates with digestate circulating in direction (26), moved by a first set (7) of mixers. The digestate is mixed as it moves in direction (26). There may be small or local mixing flows that are oblique or even backwards relative to direction (26) and disturbances where feed enters the first stage (5) or digestate exists from the first stage (5). However, the average flow is primarily in direction (26). Within a single trip of digestate around the raceway, the first stage (5) operates somewhat like a plug flow reactor in that there is a gradient in reaction products between the inlet and the outlet of the first stage (5). However, since the recirculating flow rate is larger than the feed flow rate, the first stage (5) also has some characteristics of a continuously stirred tank reactor (CSTR). A particle of recirculating substrate passes the feed inlet, on average, many times, for example 20 or more or between 20 and 30, before exiting from the first stage (5). The second stage (6) operates generally like a CSTR.

The solids content and viscosity in the first stage (5) are higher than in the second stage (6) as a result of partial digestion of the volatile solids in the feedstock in the first stage (5). As digestion continues in the second stage (6), the solids content and viscosity of the digestate are further reduced, which makes it easier to mix the digestate. A portion of the digestate from the second stage (6) can be recirculated to the first stage tank if needed to reduce the solids content in the first stage (5) with difficult-to-digest substrates. Typically the volume of the first stage (5) is 40 to 50% of the total volume of the digester (25).

In the system 100 of FIGS. 1 and 2, one or more stackable substrates (A) are received in a solids feeder (1). Substrates with a solids content in excess of 40% dried solids (DS) can be fed. The solids feeder (1) can be loaded with a front end loader, or it can be installed below grade such that it can be fed from a dump truck. The solids feeder (1) may provide enough storage volume for about 12 to 24 hours worth of stackable substrate (A) to be fed to the digester tank (25). Solids feeders (1) such as those sold by UTS Products GmbH of Germany have a live rubber belt bottom resting on closely spaced rollers. The stackable substrate (A), alternatively called feedstock, is driven forward and passed through milling drums that grind and loosen the stackable substrate (A), which then drops onto a belt or chain conveyor (2). The conveyor (2) drops the stackable substrate (A) into the hopper of an auger (3). The auger (3) discharges the stackable substrate (A) about 0.6 m below the free surface of the digestate in the first stage (5). This inhibits biogas escape from the digester (25). The solids feeder (1) may contain load cells that are used to quantify the amount of stackable substrate (A) fed. This feature can be used in an automatic feed control system. The solids feeder (1) may be programmed for automatic intermittent feed, supplying an equal fraction of the total daily feed at predetermined time intervals. For example, substrate may be fed for 10 minutes once every 30 or 40 minutes, of for 15 minutes once every hour.

One or more pumpable substrates (B), with lower solids content than the stackable substrates (A), may be fed to the digester (25) alone or in combination with one or more stackable substrates (A). Examples of pumpable substrates (B) include cow or pig manure, food waste slurry, and restaurant grease. Pumpable substrates (B) are stored in a mixed tank (4) and fed with a pump (15), such as a centrifugal chopper pumps or a positive displacement pump. The pumpable substrate (B) is preferably fed when the first set of mixers (7) are operating. The inlet point for pumpable substrates (B) may be between the inlet point for the stackable substrates (A) feed point and a first mixer (7) downstream of the inlet point for the stackable substrates (A). The digester (25) preferably also receives a daily dose of micronutrients, which may be diluted and sprayed onto the solids stackable substrate (A).

The first set of mixers (7) preferably all operate at the same time but intermittently. Mixer operation preferably coincides with feeding stackable substrates (A). The first set of mixers (7) may operate, for example, for 15 minutes every hour or 10 minutes every 30 or 40 minutes, or according to other mixing regimes that can be preset in a programmable logic controller. There can be between three and six mixers in the first set of mixers (7), depending on the tank (27) diameter and the solids content of the digestate. Tank (27) sizes may range, for example, from a 26 m outer diameter with a 16 m diameter internal wall (28), to as large as a 46 m outer tank diameter with a 32 m diameter internal wall (28). The first stage (5) may range from 5 m to 7 m in width.

The tank (27) is covered, usually with a membrane cover or concrete, or with a combination of these covers. In FIG. 1, the first stage (5) has a concrete cover (17). The second stage (6) shown has a double membrane cover (13) that acts as a gas holder, but can also have a concrete cover. Maximum depths of the tank (27) is preferably about 12 m. The walls of the tank (27) and the internal wall (28) can be made of concrete or with coated carbon steel sections bolted together.

The preferred mixers (7) are 22 kW hydraulic power driven submersible mixers manufactured by UTS Products GmbH. These mixers (7) have three blade rotors (8) with a 960 mm diameter and operate at 170 rpm. The mixers (7) are driven by a hydraulic motor. Hydraulic power is produced by a hydraulic power unit (HPU) with a hydraulic pump and an oil reservoir and valves. The HPU is located outside of the tank (27) in an equipment room adjacent to the digester (25). The mixers (7) are mounted on square stainless steel guide columns (22). Access to a mixer (7) is through a service box (10) located on top of the mixer (7) and attached to the digester cover (17), (13). Suitable service boxes (10) are also manufactured by UTS Products GmbH.

In the first stage (5), the mixers (7) move the thick, viscous digestate in direction (26) around the endless path or raceway defined by the outer wall of tank (27) and the internal wall (28). A first mixer (7) is placed about 2 to 3 m downstream of auger (3), which provides the inlet for the stackable solids (A). This first mixer (7) is located close to the surface of the digestate, at the minimum mixer allowable depth, and has a rotor (8) higher than the rotors (8) of other mixers (7) in the first stage (5). Rotors (8) of the other mixers (7) in the first stage are placed at different heights, moving deeper the farther they are located from the first mixer (7) in the direction (26). This facilitates vertical transport of the digestate as it moves along the raceway towards the passageway (29).

The raceway configuration allows the first stage (5) to operate at a solids content and viscosity that could not be easily mixed in a circular tank. This is possible because the digestate in the first stage (5) moves primarily in a single direction (26), with some vertical mixing due to the position of the mixers (7). The first stage (5) operates as a "first in, first out", or plug-flow, reactor within a single course around the raceway. Substrate components such as proteins, sugars, starch, and fat decompose within a few hours in the first stage (5). As these components decompose, the viscosity of newly fed stackable substrates (A) decreases. Newly fed stackable substrates (A) are also blended with recirculating digestate as it moves back towards the auger (3). The more readily digestable fraction of the substrate sinks in the first stage (5) as it moves along the raceway facilitated by its loss of viscosity. This sunken fraction reaches the passageway (29) after fewer rotations around the raceway. To ensure that newly fed stackable substrate (A) makes at least one nearly complete rotation around the raceway, the auger (3) is located downstream of the passageway (29) but preferable by an angular displacement of 60 degrees or less.

The fibers and other less digestable components of the stackable substrates (A) tend to float or are pushed up by evolving biogas bubbles and stay longer in the first stage (5). As a result, there is less undigested material exiting to the second stage (6). The first stage (5) self-selects a longer solids retention time for the less digestable material. However, the fibers must be moved eventually to the second stage (6). A side stream mixing loop (31) with a chopper pump (16) takes digestate from the tank (27) through an intake (F) and returns digestate with chopped fibers to the tank (27). The intake (F) is preferably located near the free surface of the digestate, for example within one meter of the free surface. The digestate preferably returns to the tank (27) at a lower location, for example around mid depth of the tank (27). The chopped fibers are preferably not moved all of the way to the bottom of the tank (27) because there is less mixing there and it is undesirable to transfer the fibers to the second stage (6) except in a mixture with more nearly liquid digestate. The digestate with chopped fibers is preferably also returned downstream of the inlet (F). The outlet from the chopper pump (16) may be located upstream of the first mixer (7) after the auger (3), and upstream or downstream of the auger (3). This moves undigested fibers deeper in the digestate to facilitate their digestion and eventual transfer to the second stage (6). From the second stage (6) undigested fibers can be removed from the digester (25) to avoid an accumulation of non-digestible fiber in the digester (25).

Fibers and other solids may form a crust on the surface of the digestate in the first stage (5). The crust moves along the raceway following the direction of sludge circulation. The intake (F) may be connected to a crust breaker (30) installed near the surface of the digestate placed perpendicular to the raceway. Referring to FIGS. 3A and 3B, the crust breaker is generally in the form of a trough. One side (40) of the crust breaker (30) faces into the direction (26) of flow in the raceway. This side (40) has fingers (42) that break the floating crust. Broken pieces of crust and other digestate falls into the trough and are sucked out by the chopper pump (16) to be reintroduced downstream and deeper into the raceway. Crust and digestate may be allowed to temporarily accumulate in the crust breaker with a level sensor in the trough used to start and stop the chopper pump (16).

The mixers (7) have high pumping rates and move large volumes of digestate along the raceway. The flow may be in the order of 5,000 to 7,000 m3/h. The flow rate is a function of the solids content. The flow rate of in the raceway is at least about 10 times higher than the stackable substrate (A) feed flow rate. As newly fed stackable substrate (A) moves from the feed inlet point to the passageway (29) it hydrolizes and is partially digested. The front end of the raceway, just after the substrate inlets, creates acidity as volatile fatty acids are formed. As digestion of the newly fed substrate (A)) continues along the raceway, proteins and organic nitrogen are converted to ammonia as organic matter breaks down, and ammonia reacts with the carbon dioxide produced in the digestion process and forms ammonium carbonate. Ammonium carbonate is a strong buffering system that provides alkalinity. Additionally some biogas is produced from hydrogen, which also increases alkalinity. The digestate is higher in alkalinity when it returns to the substrate inlet. This brings alkalinity to where is most needed to avoid changes in pH. The local increase in alkalinity enhances process stability, which allows higher organic loadings in the first stage (5) with minimal risk of acid accumulation or pH depression.

The digester (25) may operate with as high as 17% dried solids (DS) in the first stage (5) and 14% DS in the second stage (6) within a thermophilic temperature range, for example at about 55 degrees C. In a mesophilic temperature range, for example about 38 to 40 degrees C., the maximum recommended solids content is 14% DS for the first stage (5) and 10% DS for the second stage (6). These limits are to achieve adequate mixing in both stages using the mixers (7) described above. Thermophilic operation allows higher solids content because at increased temperature the viscosity drops for the same solids content, which facilitates mixing. With high solids substrates that leave a large fraction of undigested residue (usually non degradable volatile solids), such as grass silage, dilution of the first stage (5) digestate may be required. This can be done by recirculating a portion of the lower solids content digestate from the lower half of the second stage (6). Usually in this section of the second stage (6) the solids content is lower. First stage (5) dilution can also be accomplished by returning more filtrate (H) from dewatering the second stage digestate (D) than is desired for fiber removal with biomass return (as will be described below) to the first stage.

Effluent digestate (D) is removed from the digester (25) by a pump (14). A portion of the waste digestate is permanently removed from the digester (25) to provide a mass balance of inlets and outlets. A further portion of the effluent digestate (D) is sent to a dewatering unit (18), such as a screw press, to provide additional removal of undigested fibers. Filtrate (H) from this portion of the effluent digestate (D) returns from the dewatering unit (18) through a filtrate return line (32) to the first stage (5). In this way, essentially undigestible, or poorly digestible, solids are removed from the digestate while filtrate (H) containing biomass and more readily digestible solids is retained in the digester (25).

Screw presses may have wedge wire screens with openings under 1000 microns that retain partially digested fibers and other solids. Separated solids (G) are temporarily stored in a clamp (19) and can be composted or further heat dried for use as fertilizer pellets or fuel. The dewatering unit (18) allows bacterial mass to pass with the filtrate (H). A portion of this bacterial mass is returned with the filtrate (H) to the first stage (5). This return of viable anaerobic bacteria helps extend the bacterial solids retention time and avoid washout. Removing solids while retaining bacteria is particularly beneficial in highly loaded digesters operating at relatively low hydraulic retention times, such as less than 24 days HRT for a mesophilic digester, and less than 18 days HRT for a thermophilic digester.

The daily substrate flow that enters the digester (25) must also be removed daily as biogas and separated solids (G). Therefore a waste portion (I) of the dewatering filtrate, or waste portion (J) of the effluent digestate (D), or both, is discharged. The waste portion (I) of the dewatering filtrate can be used as liquid fertilizer for land application or treated further to remove nutrients and organic matter to make it suitable for discharge if there is no land available for application.

In agricultural areas that supply crop silage for digestion, nutrients are preferably returned to the soil. This is accomplished by diverting a waste portion (J) of the effluent digestate (D) to tanker trucks (22) for land application. In some countries, digestate land application is not possible during Winter Season, and regulations require digestate storage for 180 days. When this is the case, a digestate storage tank with intermittent mixing is constructed. The waste portion (J) is regularly transferred to this tank. The storage tank is covered, for example with a gas holding membrane cover. During storage there is still some additional volatile solids destruction and biogas is produced. The gas space of the digestate storage tank is connected with the digester (25).

In the second stage (6) there are usually undigested fibers that have gone through the process. It is important to remove these fibers from the digester (25) in the effluent digestate (D). Fibers accumulate near the surface of the digestate in the second stage (6) pushed up by gas bubbles. The second stage (6) effluent digestate pumping system preferably has two inlet ports with selection between them provided by a valve (33). An upper inlet port (21) is near the surface of the digestate and removes digestate with higher fiber content. This digestate typically goes to the dewatering unit (18). A second, lower, inlet port (20) is located in the lower half of the second stage (6), preferably just above the bottom. This lower port (20) removes digestate with less fiber and lower solids content. This digestate may be treated as waste portion (J) digestate that goes to a digestate storage tank or fields for land application, or it may be returned to the first stage (5) for dilution if needed.

The digester (25) may operate with about one meter of head space above the liquid level. The head spaces of the first stage (5) and second stage (6) are connected with large openings (12) through the internal wall (28), such that the membrane cover (13) of the second stage (6) allows constant pressure storage of the gas produced in both stages. Biogas (E) is extracted from connections in the service boxes (10). This provides adequate distance from the free surface of the digestate to the gas outlet, which limits the potential for foam carryover. The gas pressure is boosted for use in engines, other combined heat and power (CHP) generation systems, or systems to upgrade the biogas to pipeline quality renewable natural gas.

The passageway (29) has an inlet near the bottom of the first stage (5). Flow through the passageway (29) may be by gravity with the first stage digestate (C) flowing through an internal riser portion (9) of the passageway into the second stage (6) driven by the differential head of the digestate in the two tanks. The free surface of the digestate is usually about 20 to 30 cm higher in the first stage (5). When the solids content of the first stage digestate (C) is higher than about 12% in mesophilic operation, it is too viscous and the small head differential across the internal wall (18) is not sufficient to overcome friction losses in the passageway (29). In this case, the flow is helped by pressurizing and injecting a controlled amount of biogas near the bottom of the riser portion (9) to create a gas lift pump. Optionally, an chopper pump my be used to transfer digestate from the first (5) to the second stage (6).

The second stage (6) operates generally like a CSTR. A second set of mixers (7) installed around the perimeter of the internal wall (18) generate a swirling motion in the second stage (6), and also provide vertical mixing as shown by the arrows in FIGS. 1 and 2. The rotors (8) are pointed toward the center of the tank (27) but with a 5 to 10 degree offset. This produces the swirl or spinning motion. The second stage (6) requires three 22 kW mixers (7) for diameters between 16 and 32 meters and depths from 8 to 12 m, when operating with 8 to 10% solids content in either the thermo- or meso-philic range. Higher solids content may require four mixers (7). If the digestate is more than 6 m deep, some rotors (8) may be placed are at a higher level. If the digestate is 6 m deep or less, all rotors (18) at located about one third up from the bottom.

In the second stage (6), digestion continues and the solids content of the digestate lowers. All second set mixers (7) operate intermittently at the same time. Mixing may occur for 10 or 15 minutes every 30 to 60 minutes, preferably and after mixing in the first stage (5) occurs. This way, the same hydraulic power units employed to power the first set of mixers (7) can be used to power the second set of mixers (7). Other mixing regimes can also be programmed in the control system depending on the type of substrate. Digestate is taken from the second stage tank (6) by pump (14) through inlet ports (20) or (21).

Anaerobic digestion is an exothermic process. In high solids digesters the significant energy density of the substrate and the reduced amount of water added for dilution result in a noticeable temperature increase compared to the temperature of the substrate (A), (B). The tank (27) has insulation on the external wall. The tank-in-tank configuration, particularly when constructed with concrete, reduces heat losses from the internal tank, as the internal wall (18) and outer ring act insulators. However, heating may be required and can be provided using hot water heating pipes installed inside the tank (27), along the outer wall and the internal wall (18). Hot water, for example from a combined heat and power (CHP) unit burning the biogas (E), is circulated through the heating pipes. Other configurations, for example with external tube-in-tube heat exchangers (HEX) with large openings are also possible. In this case second stage tank digestate is pumped from the bottom half of the tank (27) through a HEX, where heat is transferred from hot water produced by the CHP unit or a hot water boiler. Heated second stage digestate is circulated into the first stage digester. This contributes to dilute the first stage solids content and to transport heat.

The system 100 described above is merely one example of an anaerobic digestion system and is not meant to limit the invention. The invention is defined by the following claims

What is claimed is:

1. An anaerobic digester comprising,
   a) a covered cylindrical tank;
   b) an interior wall dividing the cylindrical tank into an outer portion and an undivided cylindrical inner portion; and,
   c) a passageway from the outer portion to the inner portion,
   wherein the cover of the outer portion and/or the cover of the inner portion is a concrete cover.

2. The digester or claim 1 further comprising a set of mixers spaced around the outer portion and oriented to direct digestate in one direction around the outer portion in an endless loop.

3. The digester of claim 1 wherein the outer portion has at least 40% of the volume of the digester.

4. The digester of claim 1 wherein an inlet is adapted to introduce a stackable substrate into the outer portion and further comprising a second inlet adapted to introduce a pumpable substrate into the outer portion.

5. The digester of claim 1 wherein the passageway comprises an inlet near a bottom of the interior wall side, and a riser extending upward in the inner portion such that digestate flows upwards while moving from the outer portion to the cylindrical inner portion.

6. The digester of claim 1, wherein the outer portion is ring shaped.

7. The digester of claim 1, wherein the outer portion is an undivided ring shaped outer portion.

8. The digester of claim 1, wherein the passageway passes through the interior wall from the outer portion to the inner portion.

9. The digester of claim 1, wherein the cover of the outer portion is a concrete cover and the cover of the inner portion is a membrane cover.

10. An anaerobic digester comprising:
   a) a covered cylindrical tank;
   b) an interior wall dividing the cylindrical tank into an undivided ring shaped outer portion and a cylindrical inner portion; and,
   c) a passageway from the outer portion to the inner portion;
   d) a set of mixers spaced around the undivided ring shaped outer portion and oriented to direct digestate in one direction around the ring shaped outer portion in an endless loop;
   e) an inlet for adding a substrate to the ring shaped outer portion, wherein the inlet is located downstream of the passageway by an angular displacement of 60 degrees or less from the passageway.

11. The digester of claim 10 wherein a first of the set of mixers located closest to the inlet in the one direction has a mixing blade that is located higher than the mixing blades of other mixers in the set of mixers.

12. The digester of claim 11 wherein the height of the mixing blades decreases from the height of the mixing blades of the first mixer along the one direction.

13. An anaerobic digester comprising:
   a) a covered cylindrical tank;
   b) an interior wall dividing the cylindrical tank into an undivided ring shaped outer portion and a cylindrical inner portion; and,
   c) a passageway from the outer portion to the inner portion;
   d) a side stream in which digestate is withdrawn from a location within one meter of the free surface of the digestate in the ring shaped outer portion and the withdrawn digestate is returned to the ring shaped outer portion at a lower elevation than the withdrawal location.

14. The digester of claim 13 wherein the withdrawn digestate is returned to the ring shaped outer portion at a position displaced in the one direction away from the withdrawal location.

15. The digester of claim 13 wherein the side stream comprises a chopper pump.

16. The digester of claim 13 wherein an inlet to the side stream comprises a crust breaker.

\* \* \* \* \*